US00PP27987P2

(12) United States Plant Patent
Hansen

(10) Patent No.: US PP27,987 P2
(45) Date of Patent: May 9, 2017

(54) ***BUDDLEIA* PLANT NAMED 'QUEEN OF HEARTS'**

(50) Latin Name: ***Buddleia* hybrid**
Varietal Denomination: Queen of Hearts

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 135 days.

(21) Appl. No.: 14/545,726

(22) Filed: Jun. 10, 2015

(51) Int. Cl.
*A01H 5/00* (2006.01)

(52) U.S. Cl.
USPC ..... Plt./242

(58) Field of Classification Search
USPC ..... Plt./226, 242
See application file for complete search history.

(56) References Cited

U.S. PATENT DOCUMENTS

| | | | |
|---|---|---|---|
| PP12,383 | P2 | 2/2002 | Dransfield |
| PP14,370 | P2 | 12/2003 | Turrell |
| PP17,332 | P2 | 1/2007 | Moore |
| PP19,934 | P2 | 4/2009 | Davis |
| PP19,935 | P2 | 4/2009 | Bloom |
| PP19,950 | P3 | 4/2009 | Werner |
| PP19,991 | P3 | 5/2009 | Werner |
| PP22,063 | P2 | 8/2011 | Valin |
| PP22,064 | P2 | 8/2011 | Valin |
| PP22,065 | P2 | 8/2011 | Podaras |
| PP22,066 | P2 | 8/2011 | Podaras |
| PP22,067 | P2 | 8/2011 | Podaras |
| PP22,068 | P2 | 8/2011 | Podaras |
| PP22,069 | P2 | 8/2011 | Podaras |
| PP22,080 | P2 | 8/2011 | Podaras |
| PP22,081 | P2 | 8/2011 | Podaras |
| PP22,098 | P2 | 8/2011 | Podaras |
| PP22,108 | P2 | 9/2011 | Podaras |
| PP22,109 | P2 | 9/2011 | Podaras |
| PP22,110 | P2 | 9/2011 | Podaras |
| PP22,142 | P2 | 9/2011 | Podaras |
| PP22,143 | P2 | 9/2011 | Podaras |
| PP22,144 | P2 | 9/2011 | Podaras |
| PP22,177 | P2 | 10/2011 | Podaras |
| PP22,367 | P2 | 12/2011 | Podaras |
| PP22,465 | P2 | 1/2012 | Brand |
| PP22,680 | P2 | 4/2012 | Senior |
| PP23,214 | P2 | 11/2012 | Moore |
| PP23,425 | P2 | 2/2013 | Brand |
| PP23,461 | P2 | 3/2013 | Valin |
| PP23,462 | P2 | 3/2013 | Valin |
| PP23,463 | P2 | 3/2013 | Valin |
| PP23,464 | P2 | 3/2013 | Valin |
| PP23,498 | P2 | 3/2013 | Podaras |
| PP24,015 | P3 | 11/2013 | Werner |
| PP24,016 | P3 | 11/2013 | Werner |
| PP24,030 | P3 | 11/2013 | Podaras |

OTHER PUBLICATIONS

The Buddleja Garden. Oct. 2014. http://www.buddlejagarden.co.uk/calendar14.html. accessed Dec. 20, 2016. 4 pages.*

* cited by examiner

*Primary Examiner* — Susan McCormick Ewoldt
*Assistant Examiner* — Karen Redden

(57) ABSTRACT

*Buddleia* 'Queen of Hearts' is a broadly mounded, multi-stemmed, winter-hardy butterfly bush plant with long compact flowering thyrse over a long season beginning mid-summer with sweetly-fragrant magenta red flowers that are attractively offset by medium green foliage.

1 Drawing Sheet

Botanical classification: *Buddleia* hybrid (Linnaeas, Carl von).

Variety denomination: 'Queen of Hearts'.

BACKGROUND OF THE PLANT

The present invention relates to the new and distinct Butterfly Bush plant, *Buddleia* 'Queen of Hearts' collected by the inventor in the fall of 2011 at a wholesale perennial nursery in Zeeland, Mich., USA. 'Queen of Hearts" is the result of an ongoing breeding program conducted by the inventor. The goals for this program have been to produce improved, garden-worthy plants for the ornamental plant market. The new plant, originally assigned breeder code H11-38-03, is from an open pollination of a proprietary hybrid H10-08-08 (not patented). The male parent is unknown and was from within a population of a large number of proprietary selections and named cultivars.

*Buddleia* 'Queen of Hearts' was first asexually propagated in 2012 by stem cuttings at the same nursery in Zeeland, Mich. The resultant asexually propagated plants have been found to be stable and true to type in successive generations of asexual reproduction.

BRIEF SUMMARY OF THE PLANT

*Buddleia* 'Queen of Hearts' differs from its parents as well as all other winter-hardy butterfly bush plants known to the applicant in many traits. The flower color of 'Queen of Hearts' is a distinct vibrant magenta red. The habit of 'Queen of Hearts' is a compact broad mound.

The nearest comparison plants known to the inventor include: *Buddleia* 'Attraction' (not patented), 'Harlequin' (not patented), 'Miss Molly' U.S. Plant Pat. No. 23,425, 'Miss Ruby' U.S. Plant Pat. No. 19,950 and 'Royal Red' (not patented). Compared to the female parent, HK10-202-02, is shorter and more compact and has flowers that are more magenta red.

The following Table 1 further demonstrates some comparisons with the new plant and the nearest comparison cultivars.

TABLE 1

| CULTIVAR | Leaf color | Flower color | Habit | Size (H × W) |
|---|---|---|---|---|
| 'Attraction' | gray-green | purplish-red | large mound | 240 cm × 240 cm |
| 'Harlequin' | light green with cream margin | red-purple | towering | 180 cm × 165 cm |
| 'Miss Molly' | silvery green | red-purple | flat mound | 85 cm × 140 cm |
| 'Miss Ruby' | silvery green | bright pink | mound | 100 cm × 145 cm |
| 'Queen of Hearts' | medium green | magenta red | broad mound | 130 cm × 150 cm |
| 'Royal Red' | medium green | red-purple | huge mound | 290 cm × 300 cm |

*Buddleia* 'Queen of Hearts' is a unique winter-hardy butterfly bush different from all other *Buddleia* cultivars known to the inventor based on the following combined traits:

1. Winter-hardy shrub, with multiple-stemmed, heavily-branched, short, broadly mounded habit.
2. Many-flowered compact thyrse over a prolonged season beginning mid-summer.
3. Flowers with magenta red petals.
4. Elliptic to lanceolate foliage of medium green.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
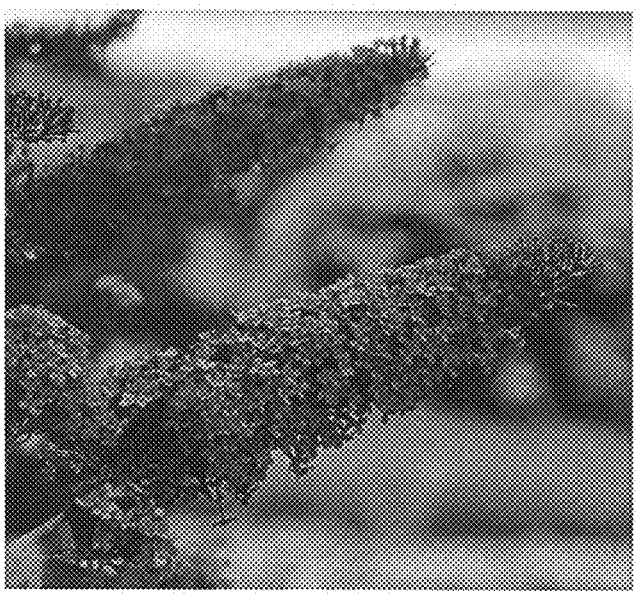
FIG. 1 shows a close-up of the flowers.
Figure 2:
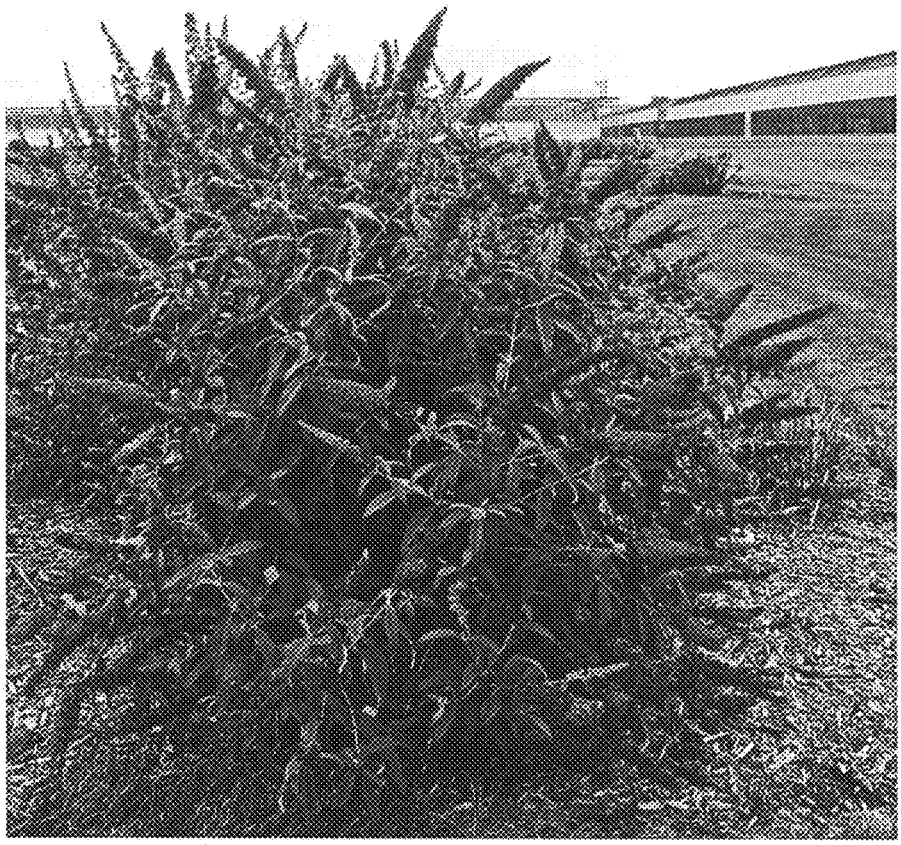
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Queen of Hearts', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand open-sun field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: Proprietary hybrid #H10-08-08 (not patented) as the female or pod parent times an unknown open-pollination as the male or pollen parent.

Propagation:

*Method.*—Softwood cuttings.

*Time to initiate roots.*—About two weeks.

*Rooting habit.*—Normal, dense and thick at base to about 1.5 cm diameter; fibrous, branching.

*Root color.*—Creamy white between RHS 159A and lighter than RHS 159 D depending on soil type; becoming woody to 1.5 cm diameter.

*Crop time.*—Under normal summer growing conditions 12 to 16 weeks to flower in a four-liter container from cutting. Plant vigor is very good.

Plant description:

*Plant shape and habit.*—Winter-hardy, herbaceous, semi-woody, well-branched shrub with about 18 thick upright and branched main stems producing an upright mound about 130 cm tall and about 150 cm wide.

*Stem.*—Rounded and woody in lower portion rounded in cross section with exfoliating bark; younger upper portion puberulent and quadrangular in cross section; strong and flexible; average about 105 cm tall from soil line to just below terminal flowers, and about 1.4 cm diameter at the base; before distal flowers about 10 branches per main stem extending at about 45° angle from horizontal in lower branches and about to 40° from horizontal in upper branches.

*Stem color.*—Just below flowers between RHS 138C and RHS 138B with heavy tinting of nearest RHS 183A especially on corner ridges and areas exposed to more direct sunlight; striated in about basal 10 cm with fissures of nearest RHS 165D and between RHS 165A and RHS 165B.

*Plant size.*—Unpinched plant with stems flowering to about 130 cm tall; overall plant about 150.0 cm wide.

*Internode.*—About 15 nodes per stem, average internode length about 6.5 cm on unpinched plant; upper nodes more pubescent than lower nodes.

*Node color.*—Same color as surrounding stem to slightly more tinted with RHS 184A.

Foliage description: Opposite, decussate; serrulate; puberulent abaxial and glabrous adaxial; elliptic to lanceolate with attenuate base and acute apex; no foliar fragrance detected.

*Leaf blade size.*—Up to about 15.5 cm long and about 5.0 cm wide, average about 12.0 cm long and about 3.0 cm wide; becoming smaller distally.

*Foliage color.*—Young expanding leaf adaxial side between RHS 138A and RHS 138B, abaxial nearest RHS 155C; mature leaves adaxial side nearest RHS 137A and abaxial lighter than RHS 145D and RHS 138D.

*Veins.*—Reticulate; abaxial raised, adaxial slightly impressed.

*Vein color.*—Young expanding adaxial nearest RHS 145D, abaxial nearest RHS 155B; mature main adaxial variable nearest RHS 193D with lateral veins same color as surrounding leaf, main abaxial nearest RHS 145C proximally and RHS 145D distally with lateral veins same color as surrounding leaf.

*Petioles.*—Glaucous and glabrous adaxial, pubescent abaxial; flatted partially top to bottom; average size about 1.0 cm long and about 2.0 mm wide at the point of attachment to stem.

*Petiole color.*—Adaxial margins nearest RHS 139B and center vein nearest RHS 193D, abaxial nearest RHS 145C.

Inflorescence description: Glomerate thyrse consisting of about 1100 self-cleaning salverform flowers; to about 34.0 cm long and 6.8 cm wide, beginning in mid-July and continuing until late October in Michigan.

*Buds*.—Narrowly spatulate, apex rounded; one day prior to opening about 11.0 mm long and about 3.5 mm in diameter in club, tube portion about 1.0 mm diameter and about 8.0 mm diameter.

*Bud color*.—Darker than RHS 71A in both tube and unopened blade portion.

*Sepals*.—Typically four, proximal two-thirds connate adpressed to corolla tube; acute apex; glabrous adaxial and pubescent abaxial; margin entire, edentate; fused in about the basal 1.5 mm and split in about the terminal 1.0 mm; forming a corolla about 2.5 mm long and about 2.0 mm across; individually less than about 1.0 mm wide at point of fusion.

*Sepal color*.—Adaxial nearest RHS 138C, abaxial nearest RHS 138B.

*Flowers fragrance*.—Pleasantly and distinctly sweet.

*Petals*.—Typically four; glabrous; fused into salver-form about 11.5 mm long, with typically straight cylindrical tube about 9.5 mm long and 1.0 mm diameter, and a flattened face about 11.0 mm across; petal blade rounded with crenate margin; blade to about 2.0 mm across and about 3.0 mm long from fused face; center 5.0 mm of flattened face portion of blade fused.

*Petal color*.—Adaxial center nearest RHS 23A in the tube surrounded by a thin irregular band of less than 0.5 mm width of nearest RHS 16A, adaxial face blades between RHS 71A and RHS 72A; abaxial tube nearest RHS 64A and abaxial petal blades nearest RHS 71A.

*Gynoecium*.—Pistil: one; about 3.5 mm long. Style: short, round, glabrous; about 1.3 mm long and less than 0.5 mm diameter; color nearest RHS 144C. Stigma: oblong, minutely puberulent; about 1.2 mm in diameter and less than 0.7 mm long; color nearest RHS 141B. Ovary: superior; globose; about 1.0 mm across at base and 2.0 mm tall; distally tapering to style; color between RHS 144A and RHS 144B.

*Androecium*.—Filaments: not produced or very short. Anthers: typically four; oblong; introrse; adnate to about mid-point of corolla tube; about 1.0 mm long and 0.5 mm wide; color nearest RHS 4D. Pollen: numerous, globose, less than 0.1 mm diameter; color nearest RHS 191C.

*Pedicel*.—Short, puberulent; about 2.0 mm long and about 0.5 mm diameter; color nearest RHS 138B.

*Peduncle*.—Quadrangular, pubescent, flexible and strong; to about 34.0 cm long.

*Peduncle color*.—Between RHS 138C and RHS 138B.

*Fruit*.—Moderate fruit set; oblong with acute apex; glabrous, bi-valved, septicidal capsule; about 6.0 mm long and about 1.5 mm across.

*Fruit color*.—As maturing between RHS 144C and RHS 144D; when mature and dehiscing between RHS 165A and RHS 165B.

*Seed*.—Elongated ellipse with sharply acute ends; less than about 2.0 mm long and about 0.1 mm diameter in center.

*Seed color*.—Nearest RHS 200A.

Disease resistance: Resistance to deer browsing has been observed. Further resistance beyond that of other known winter-hardy butterfly bush cultivars has not been noted. The plant grows best with plenty of moisture and adequate drainage, but is able to tolerate some drought when mature.

Hardiness at least from USDA zone 6 through 10.

I claim:

1. A new cultivar of winter-hardy butterfly bush plant *Buddleia* plant named 'Queen of Hearts' as herein illustrated and described, suitable for potted plant culture, landscaping as a specimen or en masse or as cut flower purposes.

* * * * *